United States Patent [19]

Chou et al.

[11] Patent Number: 4,873,264

[45] Date of Patent: Oct. 10, 1989

[54] NOVEL PESTICIDAL 1-(ALKYL-PHENOXY-ARYL)-3-BENZOYL UREAS AND PROCESS FOR PREPARATION

[75] Inventors: David T. Chou, Raleigh; Paul A. Cain, Cary, both of N.C.

[73] Assignee: Rhone-Poulenc Nederlands B.V., Amstelveen, Netherlands

[21] Appl. No.: 168,625

[22] Filed: Mar. 7, 1988

Related U.S. Application Data

[63] Continuation of Ser. No. 495,331, May 20, 1983, abandoned, which is a continuation-in-part of Ser. No. 393,553, Jun. 30, 1982, abandoned.

[51] Int. Cl.$^4$ .................. A01N 47/34; C07C 157/12; C07C 127/22
[52] U.S. Cl. .................. 514/594; 514/584; 514/522; 514/535; 564/23; 564/44; 558/415; 560/34; 560/18
[58] Field of Search .................. 564/44, 23; 514/584, 514/594

[56] References Cited

U.S. PATENT DOCUMENTS

| | | | |
|---|---|---|---|
| 3,933,908 | 1/1976 | Wellinga et al. | 564/44 |
| 3,992,553 | 11/1976 | Sirrenberg et al. | 424/304 |
| 4,005,223 | 1/1977 | Sirrenberg et al. | 424/322 |
| 4,041,177 | 8/1977 | Sirrenberg et al. | 424/322 |
| 4,064,267 | 12/1977 | Sirrenberg et al. | 424/304 |
| 4,068,002 | 1/1978 | Sirrenberg et al. | 424/322 |
| 4,123,449 | 10/1978 | Sirrenberg et al. | 260/453 AR |
| 4,194,005 | 3/1980 | Sirrenberg et al. | 424/304 |
| 4,350,706 | 9/1982 | Brouwer et al. | 564/44 X |
| 4,399,152 | 8/1983 | Brouwer et al. | 564/44 X |
| 4,426,385 | 1/1984 | Cain | 564/44 |
| 4,508,734 | 4/1985 | Lange et al. | 564/44 X |
| 4,533,676 | 8/1985 | Sirrenberg et al. | 564/44 X |

FOREIGN PATENT DOCUMENTS

| | | | |
|---|---|---|---|
| 17484 | 10/1980 | European Pat. Off. | |
| 44410 | 1/1982 | European Pat. Off. | 564/44 |
| 57888 | 8/1982 | European Pat. Off. | 564/44 |
| 74074 | 3/1983 | European Pat. Off. | 564/44 |
| 0098158 | 1/1984 | European Pat. Off. | |
| 0016475 | 7/1968 | Japan | 71/120 |
| 0038357 | 3/1980 | Japan | 564/44 |
| 0025144 | 3/1981 | Japan | 564/44 |
| 0092857 | 7/1981 | Japan | 564/44 |
| 0002258 | 1/1982 | Japan | 564/44 |
| 0002259 | 1/1982 | Japan | 564/44 |
| 149261 | 7/1982 | Japan | |
| 2062634 | 5/1981 | United Kingdom | 564/44 |
| 2083360 | 3/1982 | United Kingdom | |

OTHER PUBLICATIONS

Chemical Abstracts, vol. 95, No. 23, p. 645, Abstract No. 203586e, Dec. 7, 1981.

*Primary Examiner*—Charles F. Warren
*Assistant Examiner*—Carolyn S. Greason
*Attorney, Agent, or Firm*—Morgan & Finnegan

[57] ABSTRACT

Novel 1-(alkylphenoxyphenyl)-3-benzoyl ureas and a process for their preparation are provided. The novel ureas are useful as the active toxicant in pesticidal composition.

6 Claims, No Drawings

NOVEL PESTICIDAL 1-(ALKYL-PHENOXY-ARYL)-3-BENZOYL UREAS AND PROCESS FOR PREPARATION

This is a continuation of co-pending application Ser. No. 495,331, filed on May 20, 1983, now abandoned, which is a continuation-in-part of U.S. patent application Ser. No. 393,553 filed June 30, 1982.

FIELD OF INVENTION

This invention relates in general to novel 1-(alkylphenoxyaryl)-3-benzoyl ureas and to a process for their preparation. In one aspect, this invention relates to benzoyl ureas which are useful as pesticides.

BACKGROUND OF THE INVENTION

Prior to the present invention a few benzoyl ureas had been reported in the patent literature as having pesticidal activity. For example, U.S. Pat. No. 3,992,553 which issued on Nov. 16, 1976, and U.S. Pat. No. 4,041,177 which issued on Aug. 9, 1977, both disclosed certain benzoylureido-diphenyl ethers which were indicated to possess insecticidal properties. Similarly, U.S. Pat. Nos. 3,748,356 and 3,933,908 also disclosed certain substituted benzoyl ureas and stated that the compositions had strong insecticidal activity. U.S. Pat. No. 4,148,902 which issued Apr. 10, 1979 discloses substituted ((phenylamino)carbonyl) pyridine carboxamides and claims a method of controlling insects in addition to the compositions themselves. Additional disclosures of benzoyl ureas in the patent literature are found in U.S. Pat. Nos. 4,166,124; 4,083,977; 4,160,834; 4,264,605; 4,064,267; and 4,005,223; 4,123,449; 4,068,002; 4,194,005; 4,275,077; 4,173,639; 3,989,842; Ger. Offen. 2,901,334 (EP 013-414); and DE 3,104,407 (EP 57-888).

Accordingly, one or more of the following objects can be achieved by the practice of this invention. It is an object of this invention to provide novel 1-(alkylphenoxyaryl)-3-benzoyl ureas. Another object of this invention is to provide certain 1-(alkylphenoxyphenyl)-3-benzoyl ureas which exhibit excellent insecticidal activity. A still further object of this invention is to provide novel benzoyl ureas, such as, 1-[2,4-dimethylphenoxy-3,6-dimethyl-5-chlorophenyl]-3-(2,6-difluorobenzoyl) urea, 1-[4-(2,5-dimethyl-4-chlorophenoxy)-3,6-dimethyl-5-chlorophenyl]-3-(2,6-difluorobenzoyl)urea, etc. Another object is to provide processes for the preparation of the novel benzoyl ureas. A further object is to provide novel pesticidal compositions containing the novel benzoyl ureas as the active toxicant. Another object of the invention is to provide a method for controlling pests by the application of the novel pesticidal compositions. These and other objects will readily become apparent to those skilled in the art in the light of the teachings herein set forth.

SUMMARY OF THE INVENTION

In its broad aspect the invention relates to novel 1-(alkylphenoxyaryl)-3-benzoyl ureas, pesticidal compositions containing the same, and processes for their preparation and use. The benzoyl ureas of this invention can be represented by the following formula:

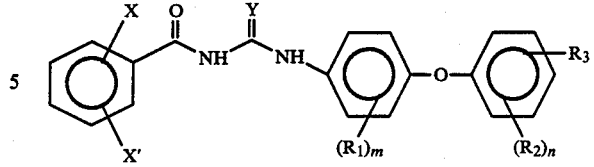

Wherein
X, X' are independently hydrogen, halogen, $C_1$–$C_4$ alkyl, haloalkyl, polyhaloalkyl, alkoxy, polyhaloalkoxy
Y represents oxygen or sulfur;
m, n are 0–4;
$R_1$ represents halogen, $C_1$–$C_4$ alkyl, haloalkyl, polyhaloalkyl, alkoxy,
$R_2$ represents halogen, $C_1$–$C_4$ alkyl, polyhaloalkyl, polyhaloalkoxy, $C_1$–$C_8$ alkylsulfonyl, $C_1$–$C_8$ alkoxy, $C_1$–$C_8$ alkylthio, $C_1$–$C_8$ dialkylamino, CN, $NO_2$, $CO_2R_4$, $CONHR_4$ wherein $R_4$ represents $C_1$–$C_8$ alkyl; and
represents $C_1$–$C_{12}$ alkyl, with the proviso that m may not be 0 or 1 when n is less than 2.

DETAILED DESCRIPTION OF THE INVENTION

As indicated above, the invention relates to novel 1-(alkyl-phenoxyaryl)-3-benzoyl ureas, pesticidal compositions containing the same, and processes for their preparation and use.

Preferred benzoyl urea compounds within the broad generic formula 1 are those having the formulas:

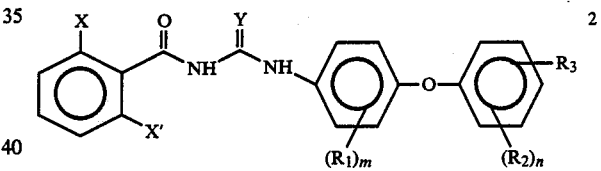

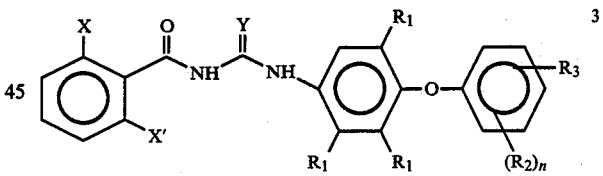

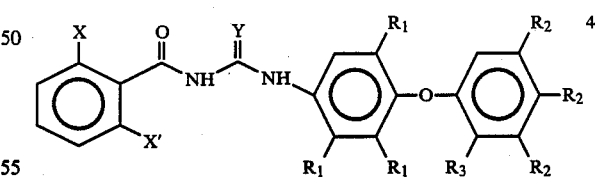

wherein X, $X^1$, Y, $R_1$, $R_2$, $R_3$, n and m are as indicated above.

Particularly preferred benzoyl ureas are those of the formulas:

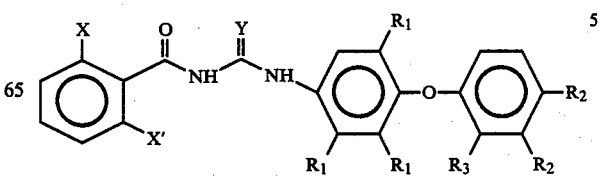

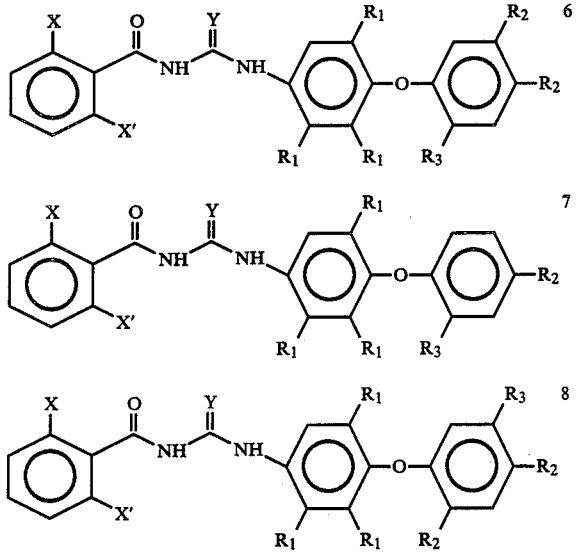

Wherein X, X', Y, R1, R2 and R3 are as indicated above.

The following benzoyl urea compounds are illustrative of those encompassed by the above formulas and which can be prepared by the practice of this invention:

1-[4-(2-methyl-3,4-dichlorophenoxy)-3,6-dimethyl-5-chlorophenyl]-3-(2,6-difluorobenzoyl)urea,
1-[4-(2-methyl-3,4-dichlorophenoxy)-3,6-dimethyl-5-chlorophenyl]-3-(2-chlorobenzoyl)urea,
1-[4-(2-methylphenoxy)-3,6-dimethyl-5-chlorophenyl]-3-(2,6-difluorobenzoyl)urea,
1-[4-(2-methylphenoxy)-3,6-dimethyl-5-chlorophenyl]-3-(2,6-dichlorobenzoyl)urea,
1-[4-(2-methylphenoxy)-3,6-dimethyl-5-chlorophenyl]-3-(2-chlorobenzoyl)urea,
1-[4-(2-methylphenoxy)-3,6-dimethyl-5-chlorophenyl]-3-(2-chlorobenzoyl)thiourea,
1-[4-(2-methylphenoxy)-3,6-dimethyl-5-chlorophenyl]-3-(2-methylbenzoyl)thiourea,
1-[4-(2-methylphenoxy)-2,3,5,6-tetramethylphenyl]-3-(2,6-dimethylbenzoyl)urea,
1-[4-(2-methylphenoxy)-2,3,5,6-tetramethylphenyl]-3-(2,6-methylbenzoyl)thiourea,
1-[4-(2-methylphenoxy)-2,3,5,6-tetramethylphenyl]-3-(2,6-difluorobenzoyl)urea,
1-[4-(2-methylphenoxy)-2,3,5,6-tetramethylphenyl]-3-(2,6-dichlorobenzoyl)urea,
1-[4-(2-methylphenoxy)-2,3,5-trimethylphenyl]-3-(2,6-dichlorobenzoyl)urea,
1-[4-(2-methylphenoxy)-3,5-dichlorophenyl]-3-(2,6-difluorobenzoyl)urea,
1-[4-(2-methyl-4-bromophenoxy)-3,6-dimethyl-5-chlorophenyl]-3-(2,6-difluorobenzoyl)urea,
1-[4-(2-methyl-4-bromophenoxy)-3,6-dimethyl-5-chlorophenyl]-3-(2-chlorobenzoyl)urea,
1-[4-(2-methyl-4-bromophenoxy)-3,6-dimethyl-5-chlorophenyl]-3-(2-chlorobenzoyl)thiourea,
1-[4-(2-methyl-4-bromophenoxy)-3,6-dimethyl-5-chlorophenyl]-3-(2-methylbenzoyl)thiourea,
1-[4-(2-methyl-4-bromophenoxy)-2,3,5,6-tetramethylphenyl]-3-(2,6-difluorobenzoyl)urea,
1-[4-(2-methyl-4-bromophenoxy)-2,3,5-tetramethylphenyl]-3-(2,6-difluorobenzoyl)urea,
1-[4-(2-methyl-4-bromophenoxy)-3,5-dimethylphenyl]-3-(2,6-difluorobenzoyl)urea,
1-[4-(2-methyl-4-bromophenoxy)-3,5-dichlorophenyl]-3-(2-chlorobenzoyl)urea,
1-[4-(2-bromo-4-methylphenoxy)-3,6-dimethyl-5-chlorophenyl]-3-(2,6-difluorobenzoyl)urea,
1-[4-(2-bromo-4-methylphenoxy)-3,6-dimethyl-5-chlorophenyl]-3-(2-chlorobenzoyl)urea,
1-[4-(2-bromo-4-methylphenoxy)-2,3,5,6-tetramethylphenyl]-3-(2-chlorobenzoyl)urea,
1-[4-(2-bromo-4-methylphenoxy)-3,5-dichlorophenyl]-3-(2,6-difluorobenzoyl)urea,
1-[4-(2-bromo-4-methylphenoxy)-3,5-dimethylphenyl]-3-(2-methylbenzoyl)thiourea,
1-[4-(2-methyl-4-t-butylphenoxy)-3,6-dimethyl-5-chlorophenyl]-3-(2,6-difluorobenzoyl)urea,
1-[4-(2-methyl-4-t-butylphenoxy)-3,6-dimethyl-5-chlorophenyl]-3-(2-chlorobenzoyl)urea,
1-[4-(2-methyl-4-t-butylphenoxy)-2,3,5,6-tetramethylphenyl]-3-(2,6-difluorobenzoyl)urea,
1-[4-(2-methyl-4-t-butylphenoxy)-3,5-dichlorophenyl]-3-(2-methylbenzoyl)thiourea,
1-[4-(2-methyl-4-chlorophenoxy)-3,6-dimethyl-5-chlorophenyl]-3-(2,6-difluorobenzoyl)urea,
1-[4-(2-methyl-4-chlorophenoxy)-3,5-dichlorophenyl]-3-(2-methylbenzoyl)thiourea,
1-[4-(2-methyl-4-chlorophenoxy)-2,3,5,6-tetramethylphenyl]-3-(2,6-difluorobenzoyl)urea,
1-[4-(2-methyl-4-chlorophenoxy)-3,6-dimethyl-5-chlorophenyl]-3-(2,6-dimethoxybenzoyl)urea,
1-[4-(4-nonylphenoxy)-3,6-dimethyl-5-chlorophenyl]-3-(2,6-difluorobenzoyl)urea,
1-[4-(4-nonylphenoxy)-2,3,5,6-tetramethylphenyl]-3-(2-chlorobenzoyl)thiourea,
1-[4-(4-nonylphenoxy)-3,5-dichlorophenyl]-3-(2,6-difluorobenzoyl)urea,
1-[4-(4-nonylphenoxy)-3,5-dimethylphenyl]-3-(2-methylbenzoyl)urea,
1-[4-(2-chloro-4-methylphenoxy)-3,6-dimethyl-5-chlorophenyl]-3-(2,6-difluorobenzoyl)urea,
1-[4-(2-chloro-4-methylphenoxy)-3,6-dimethyl-5-chlorophenyl]-3-(2-chlorobenzoyl)thiourea,
1-[4-(2-chloro-4-methylphenoxy)-3,5-dichlorophenyl]-3-(2,6-difluorobenzoyl)urea,
1-[4-(2-chloro-4-methylphenoxy)-2,3,5,6-tetramethylphenyl]-3-(2,6-difluorobenzoyl)urea,
1-[4-(3,4,5-trimethylphenoxy)-3,6-dimethyl-5-chlorophenyl]-3-(2,6-difluorobenzoyl)urea,
1-[4-(3,4,5-trimethylphenoxy)-3,6-dimethyl-5-chlorophenyl]-3-(2-chlorobenzoyl)thiourea,
1-[4-(3,4,5-trimethylphenoxy)-2,3,5,6-tetramethylphenyl]-3-(2-methylbenzoyl)thiourea,
1-[4-(3,4,5-trimethylphenoxy)-3,5-dichlorophenyl]-3-(2,6-difluorobenzoyl)urea,
1-[4-(2,3,5-trimethylphenoxy)-3,6-dimethyl-5-chlorophenyl]-3-(2,6-dimethoxybenzoyl)urea,
1-[4-(2,3,5-trimethylphenoxy)-2,3,5,6-tetramethylphenyl]-3-(2,6-difluorobenzoyl)urea,
1-[4-(2,3,5-trimethylphenoxy)-3-i-propylphenyl-3-(2-methylbenzoyl)thiourea,
1-[4-(2,3,5-trimethylphenoxy)-3-trifluoromethylphenyl]-3-(2,6-difluorobenzoyl)urea,
1-[4-(2-methyl-4-trifluoromethylphenoxy)-3,6-dimethyl-5-chlorophenyl]-3-(2,6-difluorobenzoyl)urea,
1-[4-(2-methyl-4-trifluoromethylphenoxy)-3,6-dimethyl-5-chlorophenyl]-3-(2-chlorobenzoyl)thiourea,
1-[4-(2-methyl-4-trifluoromethylphenoxy)-3,5-dichlorophenyl]-3-(2,6-dimethoxybenzoyl)urea, 1-[4-(2-methyl-4-trifluoromethylphenoxy)-2,3,5-trimethylphenyl]-3-(2-methylbenzoyl)thiourea,
1-[4-(2,4-dimethylphenoxy)-2,3,6-trimethylphenyl]-3-(2-chlorobenzoyl)urea,
1-[4-(3,5-dimethylphenoxy)-2,6-dimethylphenyl]-3-(2,6-difluorobenzoyl)urea,
1-[4-(2-methyl-4-methoxyphenoxy)-3,6-dimethyl-5-chlorophenyl]-3-(2,6-difluorobenzoyl)urea,
1-[4-(2-methyl-4-dimethylaminophenoxy)-3,6-dimethyl-5-chlorophenyl]-3-(2,6-difluorobenzoyl)urea,
1-[4-(2-methyl-4-methylthiophenoxy)-3,6-dimethyl-5-chlorophenyl]-3-(2,6-difluorobenzoyl)urea,
1-[4-(2-methyl-4-methylsulfonylphenoxy)-3,6-dimethyl-5-chlorophenyl]-3-(2,6-difluorobenzoyl)urea,
1-[4-(2-methyl-4-dimethylaminophenoxy)-3,5-dimethylphenyl]-3-(2-methylbenzoyl)urea,
1-[4-(2-methyl-4-methoxyphenoxy)-3-chloro-6-methylphenyl]-3-(2-methylbenzoyl)urea,
1-[4-(2-methyl-4-methoxyphenoxy)-3,6-dimethyl-5-chlorophenyl]-3-(3,4-dichlorobenzoyl)urea,
1-[4-(2,3-dimethyl-4-bromophenoxy)-3,6-dimethyl-5-chlorophenyl]-3-(2-chlorobenzoyl)urea,
1-[4-(2,5-dimethyl-4-chlorophenoxy)-3,6-dimethyl-5-chlorophenyl]-3-(2,6-difluorobenzoyl)urea,
1-[4-(2,5-dimethylphenoxy)-3,6-dimethyl-5-chlorophenyl]-3-(2,6-difluorobenzoyl)urea,
1-[4-(2,5-dimethylphenoxy)-3,6-dimethyl-5-chlorophenyl]-3-(2-chlorobenzoyl)urea,
1-[4-(2,5-dimethyl-4-ethoxycarbonylphenoxy)-3-6-dimethyl-5-chlorophenyl]-3-(2,6-difluorobenzoyl)urea,
1-[4-(2,5-dimethyl-4-ethoxycarbonylphenoxy)-3,6-dimethyl-5-chlorophenyl]-3-(2-chlorobenzoyl)urea,
1-[4-(2-methyl-4-trifluoromethylphenoxy)-3,6-dimethyl-5-chlorophenyl]-3-(2-chlorobenzoyl)urea,
1-[4-(2,5-dimethyl-4-trifluoromethylphenoxy)-3,6-dimethyl-5-chlorophenyl]-3-(2,6-difluorobenzoyl)urea,
1-[4-(2,5-dimethyl-4-trifluoromethylphenoxy)-3,6-dimethyl-5-chlorophenyl]-3-(2-chlorobenzoyl)urea,
1-[4-(2,5-dimethyl-4-trifluoromethoxyphenoxy)-3,6-dimethyl-5-chlorophenyl]-3-(2,6-difluorobenzoyl)urea,
1-[4-(2,5-dimethyl-4-trifluoromethylphenoxy)-3,6-dimethyl-5-chlorophenyl]-3-(2-chlorobenzoyl)urea,
1-[4-(2,5-dimethyl-4-methoxyphenoxy)-3,6-dimethyl-5-chlorophenyl]-3-(2,6-difluorobenzoyl)urea,
1-[4-(2,5-dimethyl-4-methoxyphenoxy)-3,6-dimethyl-5-chlorophenyl]-3-(2-chlorobenzoyl)urea,
1-[4-(3,5-dimethyl-4-chlorophenoxy)-3,6-dimethyl-5-chlorophenyl]-3-(2,6-difluorobenzoyl)urea,
1-[4-(2,4,5-trimethylphenoxy)-3,6-dimethyl-5-chlorophenyl]-3-(2,6-difluorobenzoyl)urea,
1-[4-(2,4,5-trimethylphenoxy)-3,6-dimethyl-5-chlorophenyl]-3-(2-chlorobenzoyl)urea,
1-[4-(2,5-dimethyl-4-bromophenoxy)-3,6-dimethyl-5-chlorophenyl]-3-(2,6-difluorobenzoyl)urea,
1-[4-(2,5-dimethyl-4-cyanophenoxy)-3,6-dimethyl-5-chlorophenyl]-3-(2,6-difluorobenzoyl)urea,
1-[4-(2,5-dimethyl-4-cyanophenoxy)-3,6-dimethyl-5-chlorophenyl]-3-(2-chlorobenzoyl)urea,
1-[4-(2-methyl-4-cyanophenoxy)-3,6-dimethyl-5-chlorophenyl]-3-(2,6-difluorobenzoyl)urea,
1-[4-(2-methyl-4-cyanophenoxy)-3,6-dimethyl-5-chlorophenyl]-3-(2-chlorobenzoyl)urea,
1-[4-(2,4-dimethylphenoxy)-3,6-dimethyl-5-chlorophenyl]-3-(2,6-difluorobenzoyl)urea,
1-[4-(2,4-dimethylphenoxy)-3,6-dimethyl-5-chlorophenyl]-3-(2-chlorobenzoyl)urea,
1-[4-(2,5-dichloro-4-methylphenoxy)-3,6-dimethyl-5-chlorophenyl]-3-(2,6-difluorobenzoyl)urea,
1-[4-(2,5-dichloro-4-methylphenoxy)-3,6-dimethyl-5-chlorophenyl]-3-(2-chlorobenzoyl)urea,
1-[4-(2-methyl-4,5-dichlorophenoxy)-3,6-dimethyl-5-chlorophenyl]-3-(2,6-difluorobenzoyl)urea,
1-[4-(2-methyl-4,5-dichlorophenoxy)-3,6-dimethyl-5-chlorophenyl]-3-(2-chlorobenzoyl)urea,
1-[4-(2,5-dimethyl-4-chlorophenoxy)-3-methylphenyl]-3-(2,6-difluorobenzoyl)urea and the like.

The novel benzoyl ureas of this invention can be conveniently prepared by one or more methods. For example, the compounds of this invention may be prepared by reacting a alkylphenoxyaniline (9) with a benzoyl isocyanate or benzoyl isothiocyanate (10) according to Scheme I.

SCHEME I

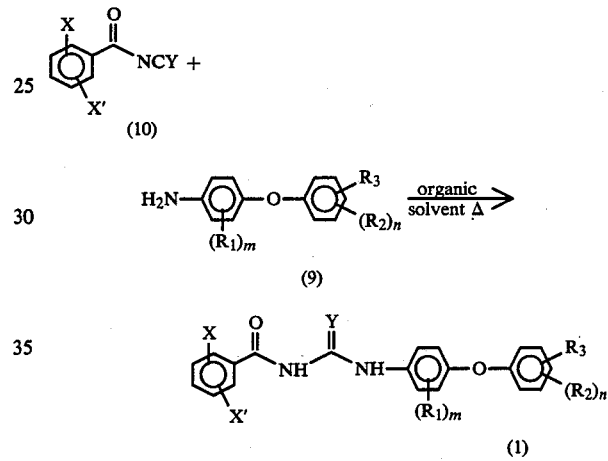

Wherein: X, X', Y, $R_1$, $R_2$, $R_3$, m, and n have the meaning given to Formula (1).

Alternatively, the novel compounds may be prepared by the reaction of an alkylphenoxyphenylisocyanate (12) with a benzamide (11) according to Scheme II.

SCHEME II

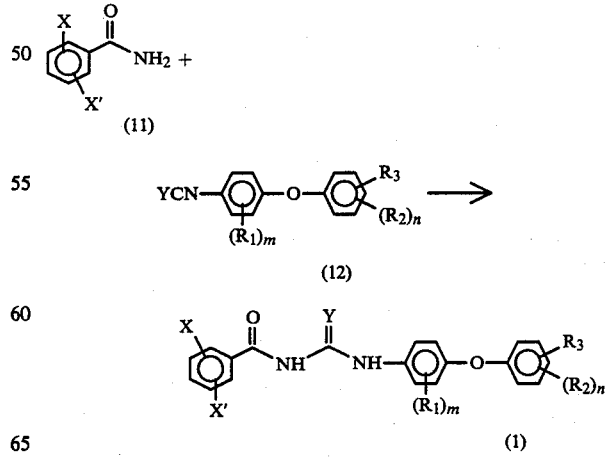

Wherein: X, X', Y, $R_1$, $R_2$, $R_3$, m, and n have the meaning given to Formula (1).

In general, the reactions illustrated in Schemes I and II can be carried out in organic solvents such as aromatic hydrocarbons halogenated hydrocarbons and the like. Solvents like toluene and 1,2-dichloroethane are preferred. These reactions proceed at temperatures ranging from room temperature to 150° C.

The intermediates shown in Schemes I and II can be prepared according to generally accepted procedures. Thus, the substituted benzoyl isocyanate (10) can be prepared from the corresponding benzamide following the general procedure of Speziale et. al., *J. Org. Chem.* 27, 3742 (1962).

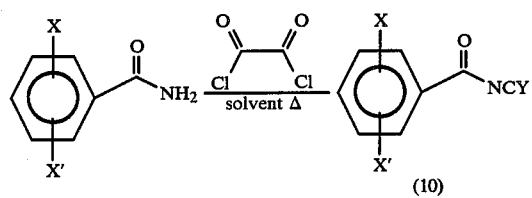

where Y = oxygen

The substituted benzoyl isothiocyanate (10) can be prepared from the corresponding acid chloride with potassium thiocyanate. This procedure in general is similar to that employed by Ambelang, et. al *J. Amer. Chem. Soc.*, 61, 632 (1937).

The aniline (9) can be prepared according to Scheme III shown below.

SCHEME III

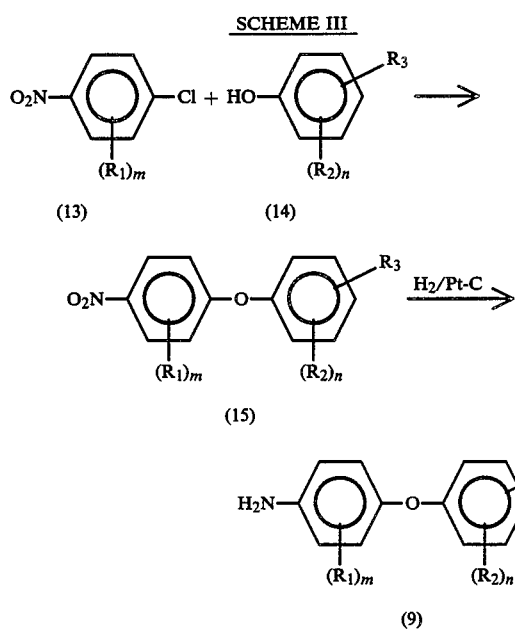

Wherein $R_1$, $R_2$, $R_3$, m and n have the meaning given to Formula 1.

The reaction of substituted chloronitrobenzene (13) with substituted phenol (14) proceeds in the presence of base at elevated temperature to give the substituted nitroether (15). The reduction of nitroether (15) to aniline (9) can be achieved under hydrogen atmosphere using a heterogeneous hydrogenation catalyst. Suitable catalyst includes platinum or palladium on carbon or Raney nickel. The pressure ranging from 20~100 PSI at ambient temperature can be applied. Suitable solvents include aromatic hydrocarbon or alcohol. The reduction of nitroether (15) to aniline (9) can also be achieved by chemical method using the procedure of E. Enders, et. al., British patent 1,456,964.

The intermediates such as substituted chloronitrobenzene and substituted phenol are available commercially or may be prepared by well known method from chemical literature.

One particular chloronitrobenzene (16) was prepared by the route outlined in Scheme IV.

SCHEME IV

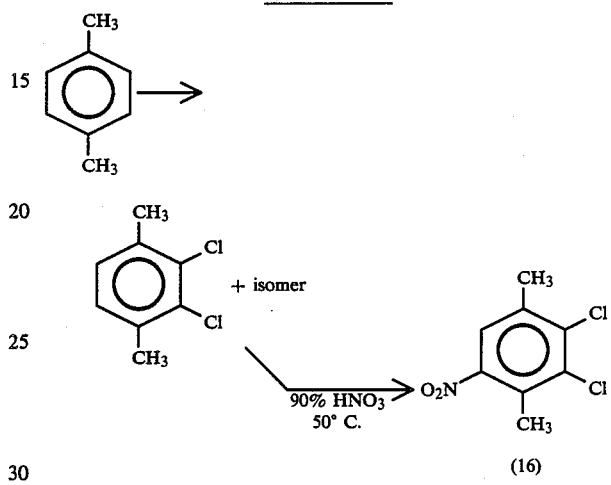

The aniline (9) can be converted to the isocyanate or isothiocyanate (12) by the reaction with phosgene or thiophosgene as shown below:

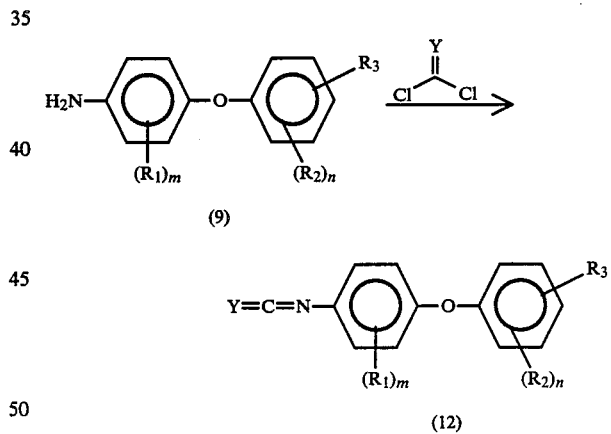

Wherein: Y, $R_1$, $R_2$, $R_3$, m, and n have the meaning given to Formula 1.

The compounds contemplated in this invention may be employed as insecticides according to methods known to those skilled in the art. Pesticidal compositions containing the compounds as the active toxicant will usually comprise a carrier and/or diluent, either liquid or solid.

Suitable liquid diluents or carriers include water, pertroleum distillates, or other liquid carriers with or without surface active agents. Liquid concentrates may be prepared by dissolving one of these compounds with a nonphytotoxic solvent such as acetone, xylene, nitrobenzene, cyclohexanone or dimethyl formamide and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does no re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fuller's earth, and the like. In the formulation of the wettable powders the aforementioned dispersing agents as well as lignosulfonates can be included.

The required amount of the toxicants comtemplated herein may be applied per acre treated in from 1to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off cause by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants. Mixtures of the active compounds may be employed if desired as well as combinations of the active compounds of this invention with other biologically active compounds or ingredients.

The following examples illustrate the best mode presently comtemplated for the practice of the invention:

EXAMPLE 1

Preparation of 4-(2,4-dimethylphenoxy)-3,6-dimethyl-5-chloronitrobenzene

To a flask equipped with condenser, stirrer, under nitrogen, was added 3,6-dimethyl-4,5-dichloronitrobenzene (50 g, 0.23 mol), 2,4-dimethylphenol (38.5 g, 0.32 mol), potassium carbonate (50 g, 0.36 mol), and dimethylformamide (125 ml). The resulting mixture was heated at 90°~100° for 72 hours. It was then cooled, filtered, and concentrated to give dark oil. It was partitioned between toluene (300 ml) and 4% sodium hydroxide (250 ml) and then separated. The organic layer was washed with water and brine, dried ($Na_2SO_4$) and concentrated to give dark oil. Solid was formed after the oil was triturated with hexane. The solid was washed with cold hexane and vacuum dried to give a tan powder (47.8 g, 0.16 mol); mp 78°~80°.

Anal: $C_{16}H_{16}ClNO_3$: Calcd: C, 62.85; H, 5.27; N, 4.58. Found: C, 63.47: H, 5.35; N, 4.49.

EXAMPLE 2

A. Preparation of 4-(2,4-dimethylphenoxy)-3,6-dimethyl-5-chloroaniline

To a solution of 4-(2,4-dimethylphenoxy)-3,6-dimethyl-5-chloronitrobenzene (25 g, 81.8 mmol) in toluene (250 ml) was added 5% platinum on carbon (1.0 g). The resulting mixture was subjected to hydrogenation at 20 psi. After 4.5 hours, the reaction mixture was filtered through celite and concentrated to given an oil (24.5 g). It turned to a pinkish solid after high vacuum drying; mp 86°~88° C.

Anal: $C_{16}H_{18}ClNO$: Calcd: C, 69.69; H, 6.53; N, 5.08. Found: C, 70.02; $H_3$ 6.60; N, 5.68.

B. Preparation of 4-(3-methyl-4-methylthiophenoxy)-3,6-dimethyl-5-chloroaniline

To a solution of 4-(3-methyl-4-methylthiophenoxy)-3,6 -dimethyl-5-chloronitrobenzene (5.0 g, 14.8 mmol) in 7.5 ml of p-dioxane was added $SnCl_2.2H_2O$ (10.0 g, 44.4 mmol) and concentrated HCl (10.5 ml). The resulting mixture was heated up to reflux for 65 min., cooled, and poured into a mixture of NaOH (20 g), $H_2O$ (50 ml), and ice (50 g). The mixture was extracted twice with toluene. The combined organic extracts were washed with 4% NaOH, $H_2O$, and brine. It was then dried ($Na_2SO_4$) and concentrated to yield a yellow oil. Solid formed after the oils was chilled and triturated with cold hexane and a trace of ethyl acetate. The solid was filtered and washed with hexane to give a beige powder (3.06 g, 9.9 mmol); mp 80°-86° C. (decomp.).

Anal: $C_{16}H_{18}ClNOS$: Calcd: C, 62.34; H, 5.89; N, 4.55. Found: C, 62.38; H, 5.89; N, 4.25.

EXAMPLE 3

Preparation of 1-(2-Chlorobenzoyl)-3-[4-(2,4-dimethylphenoxy)-3,6 -dimethyl-5-chlrophenyl]urea To a warm solution of 4.94 g (17.9 mmol) of 4-(2,4-dimethylphenoxy)-3,6-dimethyl-5-chloroaniline in 12.5 ml of toluene was added 4.21 g of 2-chlorobenzoyl isocyanate in 1.5 ml of toluene. The resulting solution was heated at 90° for 0.5 hour. It was then cooled and diluted with 5 ml of hexane. The mixture was filtered and the solid was washed with 50% hexane in toluene. A white solid (6.32 g, 13.8 mmol) was obtained after vacuum dried at 80° overnight; mp 163°-165° C.

Anal: $C_{24}H_{22}Cl_2N_2O_3$: Calcd: C, 63.03; H, 4.85; N, 6.12. Found: C, 63.33; H, 4.94; N, 6.09.

EXAMPLES 4–216

In a manner similar to that employed in the preceding examples, and using of the synthesis schemes previously disclosed, other urea compounds were prepared. The identity of the substituents on the generic formula and the analytical data are set forth in table I below:

TABLE I

1-(Alkylphenoxyaryl)-3-Benzoyl Ureas

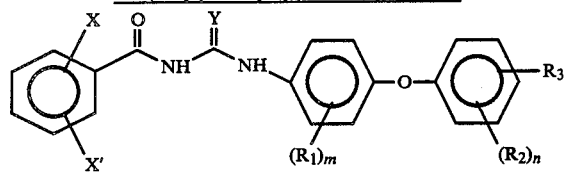

| Example | Molecular Formula | XX' | Y | R₁ | R₂ | R₃ | Calculated C | H | N | Found C | H | N |
|---|---|---|---|---|---|---|---|---|---|---|---|---|
| 1 | $C_{22}H_{16}Cl_2F_2N_2O_3$ | 2,6-F₂ | O | 3,5-Cl | 2-CH₃ | 4-CH₃ | 56.79 | 3.47 | 6.02 | 56.61 | 3.35 | 6.08 |
| 2 | $C_{22}H_{17}Cl_3N_2O_3$ | 2-Cl | O | 3,5-Cl | 2-CH₃ | 4-CH₃ | 56.97 | 3.70 | 6.04 | 56.84 | 3.61 | 6.02 |
| 3 | $C_{22}H_{16}Cl_4N_2O_3$ | 2,6-Cl₂ | O | 3,5-Cl | 2-CH₃ | 4-CH₃ | 53.03 | 3.24 | 5.62 | 52.38 | 3.15 | 5.72 |
| 4 | $C_{24}H_{22}F_2N_2O_3$ | 2,6-F₂ | O | 3,5-(CH₃)₂ | 2-CH₃ | 4-CH₃ | 67.91 | 5.23 | 6.60 | 67.23 | 5.10 | 6.62 |
| 5 | $C_{24}H_{22}ClFN_2O_3$ | 2,6-ClF | O | 3,5(CH₃)₂ | 2-CH₃ | 4-CH₃ | 65.35 | 5.03 | 6.35 | 65.22 | 5.03 | 6.29 |
| 6 | $C_{24}H_{23}ClN_2O_3$ | 2-Cl | O | 3,5(CH₃)₂ | 2-CH₃ | 4-CH₃ | 68.16 | 5.47 | 6.63 | 68.12 | 5.58 | 6.48 |
| 7 | $C_{24}H_{22}Cl_2N_2O_3$ | 2,6-Cl₂ | O | 3,5(CH₃)₂ | 2-CH₃ | 4-CH₃ | 63.02 | 4.85 | 6.13 | 58.72 | 4.16 | 6.33 |
| 8 | $C_{24}H_{22}Cl_2N_2O_3$ | 2-Cl | O | 3,5,6-CH₃ClCH₃ | 2-Ch₃ | 4-CH₃ | 63.03 | 4.85 | 6.12 | 63.33 | 4.94 | 6.09 |
| 9 | $C_{24}H_{21}Cl_3N_2O_3$ | 2,6-Cl₂ | O | 3,5,6-CH₃ClCH₃ | 2-CH₃ | 4-CH₃ | 58.61 | 4.30 | 5.70 | 58.28 | 4.21 | 5.64 |
| 10 | $C_{24}H_{21}Cl_2FN_2O_3$ | 2,6-ClF | O | 3,5,6-CH₃ClCH₃ | 2-CH₃ | 4-CH₃ | 60.64 | 4.45 | 5.89 | 60.79 | 4.42 | 5.82 |
| 11 | $C_{24}H_{21}ClF_2N_2O_3$ | 2,6-F₂ | O | 3,5,6-CH₃ClCH₃ | 2-CH₃ | 4-CH₃ | 62.82 | 4.61 | 6.10 | 62.94 | 4.88 | 6.03 |
| 12 | $C_{22}H_{15}Cl_5N_2O_3$ | 2-Cl | O | 3,5-Cl₂ | 2,3,4-CH₃ClCl | 5-CH₃ | 49.61 | 2.84 | 5.26 | 49.99 | 2.90 | 5.21 |
| 13 | $C_{22}H_{14}Cl_6N_2O_3$ | 2,6-Cl₂ | O | 3,5-Cl₂ | 2,3,4-CH₃ClCl | 5-CH₃ | 46.60 | 2.49 | 4.94 | 46.74 | 2.53 | 4.94 |
| 14 | $C_{22}H_{14}Cl_5FN_2O_3$ | 2,6-ClF | O | 3,5-Cl₂ | 2,3,4-CH₃ClCl | 5-CH₃ | 47.99 | 2.56 | 5.09 | 47.21 | 2.80 | 5.01 |
| 15 | $C_{22}H_{14}Cl_4F_2N_2O_3$ | 2,6-F₂ | O | 3,5-Cl₂ | 2,3,4-CH ClCl | 5-CH₃ | 49.47 | 2.64 | 5.24 | 49.44 | 2.74 | 5.17 |
| 16 | $C_{24}H_{22}Cl_2N_2O_2S$ | 2-Cl | S | 3,5,6-CH₃ClCH₃ | 2-CH₃ | 4-CH₃ | 60.89 | 4.68 | 5.92 | 61.13 | 4.83 | 6.05 |
| 17 | $C_{24}H_{22}Cl_2N_2O_3$ | 2-Cl | O | 3,5,6-CH₃ClCH₃ | 3-CH₃ | 5-CH₃ | 63.03 | 4.85 | 6.12 | 62.64 | 4.73 | 6.40 |
| 18 | $C_{24}H_{22}Cl_2N_2O_2S$ | 2-Cl | S | 3,6-(CH₃)₂—5-Cl | 3-CH₃ | 5-CH₃ | 60.89 | 4.68 | 5.92 | 61.12 | 4.73 | 5.94 |
| 19 | $C_{24}H_{21}Cl_3N_2O_3$ | 2,6-Cl₂ | O | 3,6-(CH₃)₂—5-Cl | 3-CH₃ | 5-CH₃ | 58.61 | 4.30 | 5.70 | 58.41 | 4.26 | 5.71 |
| 20 | $C_{24}H_{21}ClF_2N_2O_3$ | 2,6-F₂ | O | 3,6-(CH₃)₂—5-Cl | 3-CH₃ | 5-CH₃ | 62.82 | 4.61 | 6.10 | 63.23 | 4.67 | 6.08 |
| 21 | $C_{26}H_{26}Cl_2N_2O_3$ | 2-Cl | O | 3,6-(CH₃)₂—5-Cl | H | 4-t-butyl | 64.34 | 5.40 | 5.77 | 64.03 | 5.36 | 5.98 |
| 22 | $C_{26}H_{26}Cl_2N_2O_2S$ | 2-Cl | S | 3,6-(CH₃)₂—5-Cl | H | 4-t-butyl | 62.27 | 5.23 | 5.59 | 62.06 | 5.43 | 5.79 |
| 23 | $C_{26}H_{25}Cl_3N_2O_3$ | 2,6-Cl₂ | O | 3,6-(CH₃)₂—5-Cl | H | 4-t-butyl | 60.07 | 4.85 | 5.39 | 60.25 | 4.92 | 5.50 |
| 24 | $C_{26}H_{25}ClF_2N_2O_3$ | 2,6-F₂ | O | 3,6-(CH₃)₂—5-Cl | H | 4-t-butyl | 64.14 | 5.17 | 5.75 | 64.40 | 5.32 | 5.73 |
| 25 | $C_{23}H_{20}Cl_2N_2O_3$ | 2-Cl | O | 3,6-(CH₃)₂—5-Cl | H | 4-CH₃ | 62.31 | 4.55 | 6.32 | 62.22 | 4.66 | 6.23 |
| 26 | $C_{23}H_{20}Cl_2N_2O_2S$ | 2-Cl | S | 3,6-(CH₃)₂—5-Cl | H | 4-CH₃ | 60.13 | 4.39 | 6.10 | 59.84 | 4.38 | 5.98 |
| 27 | $C_{23}H_{19}Cl_3N_2O_3$ | 2,6-Cl₂ | O | 3,6-(CH₃)₂—5-Cl | H | 4-CH₃ | 57.82 | 4.01 | 5.86 | 58.09 | 4.02 | 5.85 |
| 28 | $C_{23}H_{19}ClF_2N_2O_3$ | 2,6-F₂ | O | 3,6-(CH₃)₂—5-Cl | H | 4-CH₃ | 62.10 | 4.30 | 6.30 | 62.05 | 4.41 | 6.19 |
| 29 | $C_{23}H_{20}Cl_2N_2O_3$ | 2-Cl | O | 3,6-(CH₃)₂—5-Cl | H | 2-CH₃ | 62.31 | 4.55 | 6.32 | 61.83 | 4.56 | 6.34 |
| 30 | $C_{23}H_{19}ClF_2N_2O_3$ | 2,6-F₂ | O | 3,6-(CH₃)₂—5-Cl | H | 2-CH₃ | 62.10 | 4.30 | 6.30 | 62.02 | 4.50 | 6.79 |
| 31 | $C_{23}H_{20}Cl_2N_2O_2S$ | 2-Cl | S | 3,6-(CH₃)₂—5-Cl | H | 2-CH₃ | 60.13 | 4.39 | 6.10 | 60.72 | 4.66 | 6.08 |
| 32 | $C_{23}H_{19}Cl_3N_2P_3$ | 2,6-Cl₂ | O | 3,6-(CH₃)₂—5-Cl | H | 2-CH₃ | 57.82 | 4.01 | 5.86 | 57.95 | 4.22 | 5.95 |
| 33 | $C_{23}H_{19}BrCl_2N_2O_3$ | 2-Cl | O | 3,6-(CH₃)₂—5-Cl | 4-Br | 2-CH₃ | 52.90 | 3.67 | 5.36 | 53.18 | 3.68 | 5.47 |
| 34 | $C_{23}H_{19}BrClFN_2O_2S$ | 2-F | S | 3,6-(CH₃)₂—5-Cl | 4-Br | 2-CH₃ | 52.94 | 3.67 | 5.37 | 53.13 | 3.68 | 5.37 |
| 35 | $C_{23}H_{18}BrCl_3N_2O_2$ | 2,6-Cl₂ | O | 3,6-(CH₃)₂—5-Cl | 4-Br | 2-CH₃ | 49.62 | 3.26 | 5.03 | 49.60 | 3.29 | 4.99 |
| 36 | $C_{23}H_{19}BrCl_2N_2O_2S$ | 2-Cl | S | 3,6-(CH₃)₂—5-Cl | 4-Br | 2-CH₃ | 51.32 | 3.56 | 5.20 | 51.63 | 3.53 | 5.20 |
| 37 | $C_{23}H_{18}BrClF_2N_2O_3$ | 2,6-F₂ | O | 3,6-(CH₃)₂—5-Cl | 4-Br | 2-CH₃ | 52.75 | 3.46 | 5.35 | 52.27 | 3.40 | 5.43 |
| 38 | $C_{23}H_{19}BrCl_2N_2O_3$ | 2-Cl | O | 3,6-(CH₃)₂—5-Cl | 2-Br | 4-CH₃ | 52.90 | 3.67 | 5.36 | 52.43 | 3.68 | 5.31 |
| 39 | $C_{23}H_{18}BrCl_3N_2O_3$ | 2,6-Cl₂ | O | 3,6-(CH₃)₂—5-Cl | 2-Br | 4-CH₃ | 49.62 | 3.26 | 5.03 | 49.75 | 3.23 | 5.00 |
| 40 | $C_{23}H_{18}BrClF_2N_2O_3$ | 2,6-F₂ | O | 3,6-(CH₃)₂—5-Cl | 2-Br | 4-CH₃ | 52.75 | 3.46 | 5.35 | 52.97 | 3.49 | 5.31 |
| 41 | $C_{23}H_{19}BrCl_2N_2O_2S$ | 2-Cl | S | 3,6-(CH₃)₂—5-Cl | 2-Br | 4-CH₃ | 51.32 | 3.56 | 5.20 | 50.70 | 3.55 | 5.00 |
| 42 | $C_{23}H_{19}Cl_3N_2O_3$ | 2-Cl | O | 3,6-(CH₃)₂—5-Cl | 4-Cl | 2-CH₃ | 57.82 | 4.01 | 5.86 | 57.51 | 4.00 | 5.66 |
| 43 | $C_{23}H_{18}Cl_4N_2O_3$ | 2,6-Cl₂ | O | 3,6-(CH₃)₂—5-Cl | 4-Cl | 2-CH₃ | 53.93 | 3.54 | 5.49 | 54.22 | 3.55 | 5.55 |
| 44 | $C_{23}H_{18}Cl_2F_2N_2O_3$ | 2,6-F₂ | O | 3,6-(CH₃)₂—5-Cl | 4-Cl | 2-CH₃ | 57.64 | 3.78 | 5.84 | 57.50 | 3.84 | 5.81 |
| 45 | $C_{23}H_{19}Cl_3N_2O_2S$ | 2-Cl | S | 3,6-(CH₃)₂—5-Cl | 4-Cl | 2-CH₃ | 55.94 | 3.88 | 5.67 | 55.98 | 3.94 | 5.60 |
| 46 | $C_{23}H_{19}Cl_3N_2O_3$ | 2-Cl | O | 3,6-(CH₃)₂—5-Cl | 2-Cl | 4-CH₃ | 57.82 | 4.01 | 5.86 | 58.20 | 4.17 | 5.72 |
| 47 | $C_{23}H_{18}Cl_4N_2O_3$ | 2,6-Cl₂ | O | 3,6-(CH₃)₂—5-Cl | 2-Cl | 4-CH₃ | 53.93 | 3.54 | 5.49 | 53.91 | 3.51 | 5.50 |
| 48 | $C_{23}H_{18}Cl_2F_2N_2O_3$ | 2,6-F₂ | O | 3,6-(CH₃)₂—5-Cl | 2-Cl | 4-CH₃ | 57.64 | 3.78 | 5.84 | 57.82 | 3.84 | 5.73 |
| 49 | $C_{23}H_{19}Cl_3N_2O_2S$ | 2-Cl | S | 3,6-(CH₃)₂—5-Cl | 2-Cl | 4-CH₃ | 55.94 | 3.88 | 5.67 | 55.78 | 3.91 | 5.55 |
| 50 | $C_{31}H_{36}Cl_2N_2O_3$ | 2-Cl | O | 3,6-(CH₃)₂—5-Cl | H | 4-n-C₉H₁₉ | 67.02 | 6.53 | 5.04 | 66.06 | 6.47 | 5.14 |
| 51 | $C_{31}H_{35}Cl_3N_2O_3$ | 2,6-Cl₂ | O | 3,6-(CH₃)₂—5-Cl | H | 4-n-C₉H₁₉ | 63.11 | 5.98 | 4.75 | 60.04 | 5.58 | 5.03 |
| 52 | $C_{31}H_{36}Cl_2N_2O_2S$ | 2-Cl | S | 3,6-(CH₃)₂—5-Cl | H | 4-n-C₉H₁₉ | 65.14 | 6.35 | 4.90 | 64.36 | 6.35 | 4.86 |
| 53 | $C_{25}H_{25}ClN_2O_2S$ | 2-CH₃ | S | 3,6-(CH₃)₂—5-Cl | 2-CH₃ | 4-CH₃ | 66.28 | 5.56 | 6.18 | 65.12 | 5.73 | 5.98 |
| 54 | $C_{24}H_{22}ClFN_2O_2S$ | 2-F | S | 3,6-(CH₃)₂—5-Cl | 2-CH₃ | 4-CH₃ | 63.08 | 4.85 | 6.13 | 62.91 | 4.83 | 6.14 |
| 55 | $C_{31}H_{35}ClF_2N_2O_3$ | 2,6-F₂ | O | 3,6-(CH₃)₂—5-Cl | H | 4-n-CaH₁₉ | 66.84 | 6.33 | 5.03 | 66.16 | 6.48 | 4.78 |
| 56 | $C_{27}H_{28}Cl_2N_2O_3$ | 2-Cl | O | 3,6-(CH₃)₂—5-Cl | 2-CH₃ | 4-t-butyl | 64.93 | 5.65 | 5.61 | 64.85 | 5.71 | 5.56 |
| 57 | $C_{27}H_{27}ClF_2N_2O_3$ | 2,6-F₂ | O | 3,6-(CH₃)₂—5-Cl | 2-CH₃ | 4-t-butyl | 64.74 | 5.43 | 5.59 | 64.70 | 5.73 | 5.65 |
| 58 | $C_{27}H_{28}Cl_2N_2O_2S$ | 2-Cl | S | 3,6-(CH₃)₂—5-Cl | 2-CH₃ | 4-t-butyl | 62.91 | 5.48 | 5.43 | 62.96 | 5.58 | 5.38 |
| 59 | $C_{27}H_{28}ClFN_2O_2S$ | 2-F | S | 3,6-(CH₃)₂—5-Cl | 2-CH₃ | 4-t-butyl | 64.98 | 5.66 | 5.61 | 65.24 | 5.85 | 5.52 |
| 60 | $C_{25}H_{24}Cl_2N_2O_3$ | 2-Cl | O | 3,6-(CH₃)₂—5-Cl | 2,3-(CH₃)₂ | 5-CH₃ | 63.69 | 5.13 | 5.94 | 63.68 | 5.30 | 5.99 |
| 61 | $C_{25}H_{23}Cl_3N_2O_3$ | 2,6-Cl₂ | O | 3,6-(CH₃)₂—5-Cl | 2,3-(CH₃)₂ | 5-CH₃ | 59.36 | 4.58 | 5.54 | 59.52 | 4.82 | 5.47 |
| 62 | $C_{25}H_{23}Cl_2FN_2O_3$ | 2,6-ClF | O | 3,6-(CH₃)₂—5-Cl | 2,3-(CH₃)₂ | 5-CH₃ | 61.35 | 4.74 | 5.72 | 61.49 | 4.81 | 5.77 |
| 63 | $C_{25}H_{23}ClF_2N_2O_3$ | 2,6-F₂ | O | 3,6-(CH₃)₂—5-Cl | 2,3-(CH₃)₂ | 5-CH₃ | 63.49 | 4.90 | 5.92 | 63.58 | 5.20 | 5.92 |
| 64 | $C_{25}H_{24}Cl_2N_2O_2S$ | 2-Cl | S | 3,6-(CH₃)₂—5-Cl | 2,3-(CH₃)₂ | 5-CH₃ | 61.59 | 4.96 | 5.75 | 61.78 | 5.12 | 5.77 |
| 65 | $C_{25}H_{24}ClFN_2O_2S$ | 2-F | S | 3,6-(CH₃)₂—5-Cl | 2,3-(CH₃)₂ | 5-CH₃ | 63.74 | 5.14 | 5.95 | 63.85 | 5.22 | 5.94 |
| 66 | $C_{26}H_{27}ClN_2O_2S$ | 2-CH₃ | S | 3,6-(CH₃)₂—5-Cl | 2,3-(CH₃)₂ | 5-CH₃ | 66.86 | 5.83 | 6.00 | 67.35 | 5.86 | 5.91 |
| 67 | $C_{25}H_{24}Cl_2N_2O_3$ | 2-Cl | O | 3,6-(CH₃)₂—5-Cl | 3,4-(CH₃)₂ | 5-CH₃ | 63.69 | 5.13 | 5.94 | 63.68 | 5.21 | 5.87 |
| 68 | $C_{25}H_{23}Cl_3N_2O_3$ | 2,6-Cl₂ | O | 3,6-(CH₃)₂—5-Cl | 3,4-(CH₃)₂ | 5-CH₃ | 59.36 | 4.58 | 5.54 | 59.68 | 4.80 | 5.31 |

TABLE I-continued 1-(Alkylphenoxyaryl)-3-Benzoyl Ureas

| Example | Molecular Formula | XX' | Y | R₁ | R₂ | R₃ | Calculated C | H | N | Found C | H | N |
|---|---|---|---|---|---|---|---|---|---|---|---|---|
| 69 | $C_{25}H_{23}Cl_2FN_2O_3$ | 2,6-ClF | O | 3,6-(CH₃)₂—5-Cl | 3,4-(CH₃)₂ | 5-CH₃ | 61.35 | 4.74 | 5.72 | 61.60 | 4.84 | 5.79 |
| 70 | $C_{25}H_{23}ClF_2N_2O_3$ | 2,6-F₂ | O | 3,6-(CH₃)₂—5-Cl | 3,4-(CH₃)₂ | 5-CH₃ | 63.49 | 4.90 | 5.92 | 63.35 | 4.97 | 5.83 |
| 71 | $C_{25}H_{24}Cl_2N_2O_2S$ | 2-Cl | S | 3,6-(CH₃)₂—5-Cl | 3,4-(CH₃)₂ | 5-CH₃ | 61.59 | 4.96 | 5.75 | 61.65 | 5.05 | 5.70 |
| 72 | $C_{25}H_{24}ClFN_2O_2S$ | 2-F | S | 3,6-(CH₃)₂—5-Cl | 3,4-(CH₃)₂ | 5-CH₃ | 63.74 | 5.14 | 5.95 | 64.29 | 5.17 | 5.91 |
| 73 | $C_{26}H_{27}ClN_2O_2S$ | 2-CH₃ | S | 3,6-(CH₃)₂—5-Cl | 3,4-(CH₃)₂ | 5-CH₃ | 66.86 | 5.83 | 6.00 | 67.60 | 6.13 | 6.13 |
| 74 | $C_{25}H_{24}Cl_2N_2O_3$ | 2-6 | O | 3,6-(CH₃)₂—5-Cl | H | 2-i-C₃H₇ | 63.70 | 5.13 | 5.94 | 63.94 | 5.26 | 5.87 |
| 75 | $C_{25}H_{23}ClF_2N_2O_3$ | 2,6-F₂ | O | " | H | 2-i-C₃H₇ | 63.50 | 4.90 | 5.92 | 63.36 | 5.08 | 5.80 |
| 76 | $C_{25}H_{25}ClN_2O_3$ | 2-CH₃ | O | 3,6-(CH₃)₂—5-Cl | 2-CH₃ | 4-CH₃ | 68.72 | 5.77 | 6.41 | 67.84 | 5.65 | 6.30 |
| 77 | $C_{24}H_{12}ClFN_2O_3$ | 2-F | O | " | " | " | 65.38 | 5.03 | 6.35 | 65.25 | 5.13 | 6.21 |
| 78 | $C_{25}H_{26}N_2O_3$ | 2-CH₃ | O | 3,5-(CH₃)₂ | " | " | 74.60 | 6.51 | 6.96 | 74.81 | 6.66 | 6.88 |
| 79 | $C_{25}H_{26}N_2O_2S$ | 2-CH₃ | O | " | " | " | 71.74 | 6.26 | 6.69 | 72.14 | 6.42 | 6.54 |
| 80 | $C_{24}H_{23}FN_2O_3$ | 2-F | O | " | " | " | 70.92 | 5.70 | 6.89 | 71.09 | 5.70 | 6.98 |
| 81 | $C_{24}H_{22}Cl_2N_2O_4$ | 2-Cl | O | 3,6(CH₃)₂—5-Cl | 2-OCH₃ | 4-CH₃ | 60.90 | 4.68 | 5.92 | 60.85 | 4.57 | 5.84 |
| 82 | $C_{24}H_{21}Cl_3N_2O_4$ | 2,6-Cl₂ | O | " | " | " | 56.77 | 4.17 | 5.52 | 56.53 | 4.14 | 5.37 |
| 83 | $C_{24}H_{21}Cl_2FN_2O_4$ | 2,6-ClF | O | 3,6-(CH₃)₂ | 2-OCH₃ | 4-CH₃ | 58.67 | 4.31 | 5.70 | 59.07 | 4.47 | 5.63 |
| 84 | $C_{24}H_{21}ClF_2H_2O_4$ | 2,6-F₂ | O | " | " | " | 60.70 | 4.46 | 5.90 | 60.98 | 4.19 | 5.72 |
| 85 | $C_{25}H_{25}ClN_2O_4$ | 2-CH₃ | O | " | " | " | 66.29 | 5.56 | 6.18 | 66.57 | 5.56 | 6.29 |
| 86 | $C_{24}H_{22}ClFN_2O_3S$ | 2-F | S | " | " | " | 60.95 | 4.69 | 5.93 | 60.63 | 4.58 | 5.71 |
| 87 | $C_{24}H_{23}ClN_2O_2S$ | 2-Cl | S | 3,5-(CH₃)₂ | 2-CH₃ | 4-CH₃ | 65.67 | 5.28 | 6.38 | 66.09 | 5.50 | 6.27 |
| 88 | $C_{24}H_{22}Cl_2N_2O_3S$ | 2-Cl | O | 3,6-(CH₃)₂—5-Cl | 4-SCH₃ | 3-CH₃ | 58.90 | 5.43 | 5.72 | 58.63 | 4.58 | 5.68 |
| 89 | $C_{24}H_{21}ClF_2N_2O_3S$ | 2,6-F₂ | O | " | " | " | 58.72 | 4.31 | 5.71 | 58.62 | 4.29 | 5.91 |
| 90 | $C_{26}H_{27}Cl_2N_3O_3$ | 2-Cl | O | " | 3-CH₃,4-N(CH₃)₂ | 5-CH₃ | 62.40 | 5.44 | 8.40 | 62.56 | 5.44 | 8.52 |
| 91 | $C_{26}H_{26}ClF_2N_3O_3$ | 2,6-F₂ | O | 3,6-(CH₃)₂—5-CL | 3-CH₃,4-N(CH₃)₂ | 5-CH³ | 62.22 | 5.22 | 8.37 | 62.81 | 4.93 | 8.20 |
| 92 | $C_{26}H_{26}Cl_3N_3O_3$ | 2,6-Cl₂ | O | " | " | " | 58.38 | 4.90 | 7.86 | 58.28 | 5.02 | 7.99 |
| 93 | $C_{26}H_{26}Cl_2FN_3O_3$ | 2,6-ClF | O | " | " | " | 60.24 | 5.06 | 8.10 | 60.15 | 5.13 | 7.77 |
| 94 | $C_{26}H_{27}ClFN_3O_3$ | 2-F | O | " | " | " | 64.52 | 5.62 | 8.68 | 64.57 | 5.63 | 8.64 |
| 95 | $C_{27}H_{30}ClN_3O_3$ | 2-CH₃ | O | " | " | " | 67.56 | 6.30 | 8.75 | 67.21 | 6.38 | 8.38 |
| 96 | $C_{23}H_{20}Cl_2N_2O_3$ | 2-Cl | O | 2-CH₃—5-Cl | 2-CH₃ | 4-CH₃ | 62.31 | 4.55 | 6.32 | 62.65 | 4.92 | 6.27 |
| 97 | $C_{23}H_{19}ClF_2N_2O_3$ | 2,6-F₂ | O | " | " | " | 62.10 | 4.31 | 6.30 | 62.45 | 4.78 | 6.30 |
| 98 | $C_{22}H_{17}BrCl_2N_2O_0$ | 2-Cl | O | 2-CH₃—5-Cl | 4-Br | 2-CH₃ | 51.99 | 3.37 | 5.51 | 52.51 | 3.49 | 5.56 |
| 99 | $C_{22}H_{16}BrClF_2N_2O_3$ | 2,6-F₂ | O | C-CH₃—5-Cl | 4-Br | 2-CH₃ | 51.84 | 3.16 | 5.50 | 51.70 | 3.32 | 5.37 |
| 100 | $C_{23}H_{20}BrClN_2O_3$ | 2-Cl | O | 3-CH₃ | 2-CH₃—4-Br | 6-CH₃ | 56.58 | 4.13 | 5.74 | 57.19 | 4.34 | 5.77 |
| 101 | $C_{23}H_{19}BrF_2N_2O_3$ | 2,6-F₂ | O | 3-CH₃ | 2-CH,4-Br | 6-CH₃ | 56.41 | 3.91 | 5.72 | 56.96 | 4.14 | 5.66 |
| 102 | $C_{23}H_{20}Cl_2N_2O_3$ | 2-CH₃ | O | 2-CH₃—5-Cl | 4-Cl | 2-CH₃ | 62.31 | 4.55 | 6.32 | 62.36 | 4.51 | 6.38 |
| 103 | $C_{24}H_{23}ClN_2O_3$ | 2-CH₃ | O | 2-CH₃—5-Cl | 4-CH₃ | 2-CH₃ | 68.16 | 5.48 | 6.62 | 68.37 | 5.55 | 6.53 |
| 104 | $C_{23}H_{20}ClFN_2O_3$ | 2-F | O | 2-CH₃—5-Cl | 4-CH₃ | 2-CH₃ | 64.72 | 4.72 | 6.56 | 65.29 | 4.77 | 6.63 |
| 105 | $C_{22}H_{17}Cl_3FN_2O_3$ | 2-F | O | 2-CH₃—5-Cl | 4-Cl | 2-CH₃ | 59.08 | 3.83 | 6.26 | 59.48 | 3.80 | 6.24 |
| 106 | $C_{23}H_{20}BrFN_2O_3$ | 2-F | O | 3-CH₃ | 4-Br—6-CH₃ | 2-CH₃ | 58.56 | 4.27 | 5.94 | 59.37 | 4.43 | 5.82 |
| 107 | $C_{24}H_{23}BrN_2O_3$ | 2-CH₃ | O | 3-CH₃ | 4-Br—6-CH₃ | 2-CH₃ | 61.62 | 4.96 | 5.99 | 62.83 | 5.22 | 5.85 |
| 108 | $C_{22}H_{17}BrClFN_2O_3$ | 2-F | O | 2-CH₃—5-Cl | 4-Br | 2-CH₃ | 53.74 | 3.48 | 5.70 | 53.75 | 3.59 | 5.43 |
| 109 | $C_{23}H_{20}BrClN_2O_3$ | 2-CH₃ | O | 2-CH₃—5-Cl | 4-Br | 2-CH₃ | 56.63 | 4.13 | 5.74 | 56.84 | 4.09 | 5.64 |
| 110 | $C_{23}H_{20}BrClN_2O_3$ | 2-Cl | O | 3,5-(CH₃)₂ | 4-Br | 2-CH₃ | 56.63 | 4.13 | 5.74 | 56.64 | 4.16 | 5.64 |
| 111 | $C_{23}H_{20}BrFN_2O_3$ | 2-F | O | 3,5-(CH₃)₂ | 4-Br | 2-CH₃ | 58.61 | 4.28 | 5.94 | 58.59 | 4.54 | 5.79 |
| 112 | $C_{23}H_{19}ClFN_2O_3$ | 2-Cl—6-F | O | 3,5-(CH₃)₂ | 4-Br | 2-CH₃ | 54.62 | 3.79 | 5.54 | 54.66 | 3.82 | 5.50 |
| 113 | $C_{23}H_{19}BrF_2N_2O_3$ | 2,6-F₂ | O | 3,5-(CH₃)₂ | 4-Br | 2-CH₃ | 56.46 | 3.91 | 5.72 | 56.61 | 4.30 | 5.61 |
| 114 | $C_{23}H_{19}BrClFN_2O_3$ | 2,6-ClF | O | 2,5-(CH₃)₂ | 4-Br | 2-CH₃ | 54.62 | 3.79 | 5.54 | 54.96 | 3.90 | 5.36 |
| 115 | $C_{23}H_{18}BrF_2N_2O_3$ | 2,6-F₂ | O | 2,5-(CH₃)₂ | 4-Br | 2-CH₃ | 56.46 | 3.91 | 5.72 | 56.76 | 4.07 | 5.59 |
| 116 | $C_{23}H_{20}BrClN_2O_3$ | 2-Cl | O | 2,5-(CH₃)₂ | 4-Br | 2-CH₃ | 56.63 | 4.13 | 5.74 | 56.64 | 4.20 | 5.64 |
| 117 | $C_{23}H_{20}Cl_2N_2O_3$ | 2-Cl | O | 2,5-(CH₃)₂ | 2-Cl | 4-CH₃ | 62.31 | 4.55 | 6.32 | 62.21 | 4.69 | 6.09 |
| 118 | $C_{23}H_{20}ClFN_2O_3$ | 2-F | O | 1,5-(CH₃)₂ | 2-Cl | 4-CH₃ | 64.72 | 4.55 | 6.32 | 64.93 | 4.82 | 6.54 |
| 119 | $C_{24}H_{23}ClN_2O_3$ | 2-CH₃ | O | 2,5-(CH₃)₂ | 2-Cl | 4-CH₃ | 68.16 | 5.48 | 6.62 | 68.20 | 5.61 | 6.62 |
| 120 | $C_{24}H_{23}ClN_2O_3$ | H₂ | O | 3,6-(CH₃)₂—5-Cl | 2-CH₃ | 4-CH₃ | 68.16 | 5.48 | 6.62 | 68.01 | 5.78 | 6.42 |
| 121 | $C_{23}H_{20}BrClN_2O_3$ | H₂ | O | 3,6-(CH₃)₂—5-Cl | 4-Br | 2-CH₃ | 56.63 | 4.13 | 5.74 | 57.07 | 4.56 | 5.69 |
| 122 | $C_{24}H_{22}ClFN_2O_3$ | 2-F | O | 3,6-(CH₃)₂—5-Cl | 2-CH₃ | 5-CH₃ | 65.38 | 5.03 | 6.35 | 65.74 | 5.17 | 6.25 |
| 123 | $C_{24}H_{22}Cl_2N_2O_3$ | 2-Cl | O | 3,6-(CH₃)₂—5-Cl | 2-CH₃ | 5-CH₃ | 63.03 | 4.85 | 6.12 | 63.14 | 5.13 | 6.06 |
| 124 | $C_{24}H_{21}ClF_2N_2O_3$ | 2,6-F₂ | O | 3,6-(CH₃)₂—5-Cl | 2-CH₃ | 5-CH₃ | 62.86 | 4.62 | 6.11 | 62.90 | 4.67 | 6.01 |
| 125 | $C_{25}H_{25}ClN_2O_3$ | 2-CH₃ | O | 3,6-(CH₃)₂—5-Cl | 2-CH₃ | 5-CH₃ | 68.72 | 5.77 | 6.41 | 68.94 | 5.66 | 6.27 |
| 126 | $C_{26}H_{26}Cl_2N_2O_3$ | 2-Cl | O | 2-CH₃—5-Cl | 2-CH₃ | 4-t-butyl | 64.34 | 5.40 | 5.77 | 64.93 | 5.49 | 5.73 |
| 127 | $C_{26}H_{26}ClFN_2O_3$ | 2-F | O | 2-CH₃—5-Cl | 2-CH₃ | 4-t-butyl | 66.59 | 5.59 | 5.97 | 66.81 | 5.72 | 5.91 |
| 128 | $C_{26}H_{25}ClF_2N_2O_3$ | 2,6-F₂ | O | 2-CH₃—5-Cl | 2-CH₃ | 4-t-butyl | 64.13 | 5.18 | 5.75 | 64.36 | 5.24 | 5.72 |
| 129 | $C_{27}H_{29}ClN_2O_3$ | 2-CH₃ | O | 2-CH₃—5-Cl | 2-CH₃ | 4-t-butyl | 69.74 | 6.29 | 6.02 | 69.85 | 6.41 | 5.98 |
| 130 | $C_{26}H_{26}Cl_2N_2O_3$ | 2-Cl | O | 3,6-(CH₃)₂—5-Cl | H | 2-s-butyl | 64.34 | 5.40 | 5.77 | 63.51 | 5.28 | 6.07 |
| 131 | $C_{26}H_{26}ClFN_2O_3$ | 2-F | O | 3,6-(CH₃)₂—5-Cl | H | 2-s-butyl | 66.59 | 5.59 | 5.97 | 65.73 | 6.30 | 6.36 |
| 132 | $C_{26}H_{25}Cl_2FN_2O_3$ | 2-Cl,6-F | O | 3,6-(CH₃)₂—5-Cl | H | 2-s-butyl | 62.04 | 5.00 | 5.56 | 61.06 | 4.86 | 5.79 |
| 133 | $C_{26}H_{25}ClF_2N_2O_3$ | 2,6-F₂ | O | 3,6-(CH₃)₂—5-Cl | H | 2-s-butyl | 64.13 | 5.18 | 5.75 | 64.51 | 5.35 | 5.85 |
| 134 | $C_{24}H_{22}Cl_2N_2O_3$ | 2-Cl | O | 3,6-(CH₃)₂—5-Cl | 2-CH₃ | 3-CH₃ | 63.03 | 4.85 | 6.12 | 63.35 | 5.39 | 6.36 |
| 135 | $C_{24}H_{21}Cl_2FN_2O_3$ | 2-Cl,6-F | O | 3,6-(CH₃)₂—5-Cl | 2-CH₃ | 3-CH₃ | 60.64 | 4.45 | 5.89 | 61.29 | 4.46 | 5.78 |
| 136 | $C_{24}H_{21}ClF_2N_2O_3$ | 2,6-F₂ | O | 3,6-(CH₃)₂—5-Cl | 2-CH₃ | 3-CH₃ | 62.82 | 4.61 | 6.10 | 63.04 | 4.89 | 6.21 |

TABLE I-continued 1-(Alkylphenoxyaryl)-3-Benzoyl Ureas

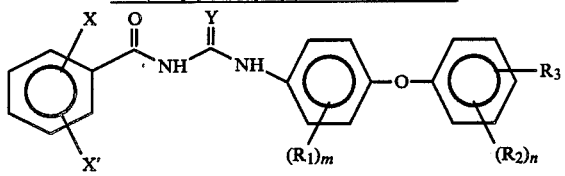

| Example | Molecular Formula | XX' | Y | R$_1$ | R$_2$ | R$_3$ | Calculated C | H | N | Found C | H | N |
|---|---|---|---|---|---|---|---|---|---|---|---|---|
| 137 | C$_{24}$H$_{21}$Cl$_3$N$_2$O$_3$ | 2-Cl | O | 3,6-(CH$_3$)$_2$—5-Cl | 2-CH$_3$—4-Cl | 3-CH$_3$ | 58.61 | 4.30 | 5.70 | 58.87 | 4.53 | 5.70 |
| 138 | C$_{24}$H$_{20}$Cl$_3$FN$_2$O$_3$ | 2-Cl,6-F | O | 3,6-(CH$_3$)$_2$—5-Cl | 2-CH$_3$—4-Cl | 3-CH$_3$ | 56.54 | 3.95 | 5.50 | 57.41 | 4.27 | 5.57 |
| 139 | C$_{24}$H$_{20}$Cl$_2$F$_2$N$_2$O$_3$ | 2,6-F$_2$ | O | 3,6-(CH$_3$)$_2$—5-Cl | 2-CH$_3$—4-Cl | 3-CH$_3$ | 58.43 | 4.09 | 5.68 | 58.59 | 4.27 | 5.65 |
| 140 | C$_{23}$H$_{20}$Cl$_2$N$_2$O$_3$ | 2-Cl | O | 3-CH$_3$ | 2-CH$_3$—4-Cl | 3-CH$_3$ | 62.31 | 4.55 | 6.32 | 62.63 | 4.62 | 6.38 |
| 141 | C$_{23}$H$_{19}$Cl$_2$FN$_2$O$_3$ | 2-Cl—6-F | O | 3-CH$_3$ | 2-CH$_3$—4-Cl | 3-CH$_3$ | 59.88 | 4.15 | 6.07 | 60.54 | 4.54 | 6.06 |
| 142 | C$_{23}$H$_{19}$ClF$_2$N$_2$O$_3$ | 2,6-F$_2$ | O | 3-CH$_3$ | 2-CH$_3$—4-Cl | 3-CH$_3$ | 62.10 | 4.30 | 6.30 | 62.55 | 4.62 | 6.27 |
| 143 | C$_{24}$H$_{21}$Cl$_3$N$_2$O$_3$ | 2-Cl | O | 3,6-(CH$_3$)$_2$—5-Cl | 2-CH$_3$—4-Cl | 5-CH$_3$ | 58.61 | 4.30 | 5.70 | 58.47 | 4.30 | 5.63 |
| 144 | C$_{24}$H$_{20}$Cl$_3$FN$_2$O$_3$ | 2-Cl,6-F | O | 3,6-(CH$_3$)$_2$—5-Cl | 2-CH$_3$—5-Cl | 5-CH$_3$ | 56.54 | 3.95 | 5.50 | 56.88 | 4.05 | 5.39 |
| 145 | C$_{24}$H$_{20}$Cl$_2$F$_2$N$_2$O$_3$ | 2,6-F$_2$ | O | 3,6-(CH$_3$)$_2$—5-Cl | 2-CH$_3$—4-Cl | 5-CH$_3$ | 58.43 | 4.09 | 5.68 | 58.72 | 4.18 | 5.68 |
| 146 | C$_{24}$H$_{21}$Cl$_3$N$_2$O$_3$ | 2-Cl | O | 3,6-(CH$_3$)$_2$—5-Cl | 3-CH$_3$—4-Cl | 5-CH$_3$ | 58.61 | 4.30 | 5.70 | 58.59 | 4.34 | 5.53 |
| 147 | C$_{24}$H$_{20}$Cl$_2$F$_2$N$_2$O$_3$ | 2,6-F$_2$ | O | 3,6-(CH$_3$)$_2$—5-Cl | 3-CH$_3$—4-Cl | 5-CH$_3$ | 58.43 | 4.09 | 5.68 | 58.38 | 4.17 | 5.53 |
| 148 | C$_{24}$H$_{21}$BrCl$_2$N$_2$O$_3$ | 2-Cl | O | 3,6-(CH$_3$)$_2$—5-Cl | 2-CH$_3$—4Br | 3-CH$_3$ | 53.75 | 3.95 | 5.22 | 53.72 | 4.03 | 5.53 |
| 149 | C$_{24}$H$_{20}$BrCl$_2$F$_2$N$_2$O$_3$ | 2,6-F$_2$ | O | 3,6-(CH$_3$)$_2$—5-Cl | 2-CH$_3$—4Br | 3-CH$_3$ | 53.60 | 3.75 | 5.21 | 53.27 | 3.78 | 5.07 |
| 150 | C$_{23}$H$_{20}$BrClN$_2$O$_3$ | 2-Cl | O | 3-CH$_3$ | 2-CH$_3$—4Br | 3-CH$_3$ | 56.63 | 4.13 | 5.74 | 56.52 | 4.22 | 5.76 |
| 151 | C$_{23}$H$_{19}$BrF$_2$N$_2$O$_3$ | 2,6-F$_2$ | O | 3-CH$_3$ | 2-CH$_3$—4Br | 3-CH$_3$ | 56.46 | 3.91 | 5.72 | 56.65 | 4.09 | 5.94 |
| 152 | C$_{23}$H$_{20}$Cl$_2$N$_2$O$_3$ | 2-Cl | O | 3-CH$_3$ | 2-CH$_3$—4-Cl | 5-CH$_3$ | 62.31 | 4.55 | 6.32 | 62.17 | 4.65 | 6.30 |
| 153 | C$_{23}$H$_{19}$Cl$_2$F$_2$N$_2$O$_3$ | 2,6-F$_2$ | O | 3-CH$_3$ | 2-CH$_3$—4-Cl | 5-CH$_3$ | 62.10 | 4.30 | 6.30 | 61.95 | 4.42 | 6.19 |
| 154 | C$_{24}$H$_{21}$BrF$_2$N$_2$O$_3$ | 2,6-F$_2$ | O | 3,5-(CH$_3$)$_2$ | 2-CH$_3$—4-Br | 3-CH$_3$ | m.p. 194~197° C. | | | | | |
| 155 | C$_{26}$H$_{25}$BrCl$_2$N$_2$O$_3$ | 2-Cl | O | 3,6-(CH$_3$)$_2$—5-Cl | 4-Br | 2-s-butyl | 55.34 | 4.46 | 4.96 | 55.49 | 4.42 | 4.87 |
| 156 | C$_{26}$H$_{24}$BrClF$_2$N$_2$O$_3$ | 2,6-F$_2$ | O | 3,6-(CH$_3$)$_2$—5-Cl | 4-Br | 2-s-butyl | 55.19 | 4.28 | 4.95 | 55.78 | 4.28 | 4.81 |
| 157 | C$_{25}$H$_{22}$ClF$_3$N$_2$O$_3$ | 2-CF$_3$ | O | 3,6-(CH$_3$)—5-Cl | 2-CH$_3$ | 4-CH$_3$ | 61.17 | 4.52 | 5.71 | 61.45 | 4.66 | 5.63 |
| 158 | C$_{25}$H$_{24}$Cl$_2$N$_2$O$_3$ | 2-Cl | O | 3,6-(CH$_3$)$_2$—5-Cl | 2,4-(CH$_3$)$_2$ | 5-CH$_3$ | 63.70 | 5.13 | 5.94 | 63.64 | 5.24 | 6.03 |
| 159 | C$_{25}$H$_{23}$ClF$_2$N$_2$O$_3$ | 2,6-F$_2$ | O | 3,6-(CH$_3$)$_2$—5-Cl | 2,4-(CH$_3$)$_2$ | 5-CH$_3$ | 63.50 | 4.90 | 5.92 | 63.75 | 5.18 | 6.63 |
| 160 | C$_{24}$H$_{21}$Cl$_3$N$_2$O$_3$ | 2-Cl | O | 3,6-(CH$_3$)$_2$—5-Cl | 2-Cl,4-CH$_3$ | 5-CH$_3$ | 58.61 | 4.30 | 5.70 | 59.19 | 4.68 | 5.60 |
| 161 | C$_{24}$H$_{20}$Cl$_2$F$_2$N$_2$O$_3$ | 2,6-F$_2$ | O | 3,6-(CH$_3$)$_2$—5-Cl | 2-Cl,4-CH$_3$ | 5-CH$_3$ | 58.43 | 4.09 | 5.68 | 58.64 | 4.36 | 5.64 |
| 162 | C$_{23}$H$_{18}$Cl$_4$N$_2$O$_4$ | 2-Cl | O | 3,6-(CH$_3$)$_2$—5-Cl | 2,4-Cl$_2$ | 5-CH$_3$ | 53.93 | 3.54 | 5.47 | 54.16 | 3.79 | 5.41 |
| 163 | C$_{23}$H$_{17}$Cl$_3$F$_2$N$_2$O$_3$ | 2,6-F$_2$ | O | 3,6-(CH$_3$)$_2$—5-Cl | 2,4-Cl$_2$ | 5-CH$_3$ | 53.77 | 3.34 | 5.45 | 53.57 | 3.42 | 5.58 |
| 164 | C$_{22}$H$_{16}$BrCl$_3$N$_2$O$_3$ | 2-Cl | O | 3,5-Cl$_2$ | 2-CH$_3$,4-Br | 5-CH$_3$ | 48.69 | 2.97 | 5.16 | 49.39 | 3.01 | 5.07 |
| 165 | C$_{22}$H$_{15}$BrCl$_2$F$_2$N$_2$O$_3$ | 2,6-F$_2$ | O | 3,5-Cl$_2$ | 2-CH$_3$,4-Br | 5-CH$_3$ | 48.56 | 2.78 | 5.15 | 49.05 | 2.86 | 5.08 |
| 166 | C$_{24}$H$_{21}$BrCl$_2$N$_2$O$_3$ | 2-Cl | O | 3,6-(CH$_3$)$_2$—5-Cl | 2-CH$_3$,4-Br | 5-CH$_3$ | 53.75 | 3.76 | 5.22 | 53.96 | 4.04 | 5.20 |
| 167 | C$_{24}$H$_{20}$BrClF$_2$N$_2$O$_3$ | 2,6-F$_2$ | O | 3,6-(CH$_3$)$_2$—5-Cl | 2-CH$_3$,4-Br | 5-CH$_3$ | 53.60 | 3.75 | 5.21 | 53.69 | 3.78 | 5.16 |
| 168 | C$_{23}$H$_{20}$Cl$_2$N$_2$O$_2$S | 2-Cl | S | 2-CH$_3$—5-Cl | 2-CH$_3$ | 4-CH$_3$ | 60.13 | 4.39 | 6.10 | 60.58 | 4.55 | 6.05 |
| 169 | C$_{22}$H$_{17}$Cl$_3$N$_2$O$_2$S | 2-Cl | S | 2-CH$_3$—5-Cl | 4-Cl | 2-CH$_3$ | 55.07 | 3.57 | 5.84 | 55.86 | 3.61 | 5.64 |
| 170 | C$_{23}$H$_{20}$Cl$_2$N$_2$O$_2$S | 2-CH$_3$ | S | 2-CH$_3$—5-Cl | 4-Cl | 2-CH$_3$ | 60.13 | 4.39 | 6.10 | 60.14 | 4.32 | 6.08 |
| 171 | C$_{24}$H$_{23}$BrN$_2$O$_2$S | 2-CH$_3$ | S | 3-CH$_3$ | 2-CH$_3$,4-Br | 6-CH$_3$ | 59.58 | 4.79 | 5.79 | 60.48 | 5.04 | 5.71 |
| 172 | C$_{22}$H$_{17}$BrCl$_2$N$_2$O$_2$S | 2-Cl | S | 2-CH$_3$,5-Cl | 4-Br | 2-CH$_3$ | 50.40 | 3.27 | 5.34 | 50.32 | 3.37 | 5.22 |
| 173 | C$_{23}$H$_{20}$BrClN$_2$O$_2$S | 2-Cl | S | 3-CH$_3$ | 2-CH$_3$—4-Br | 6-CH$_3$ | 54.78 | 4.00 | 5.56 | 55.82 | 4.37 | 5.04 |
| 174 | C$_{24}$H$_{23}$ClN$_2$O$_2$S | H$_2$ | S | 3,6-(CH$_3$)$_2$,5-Cl | 2-CH$_3$ | 4-CH$_3$ | 65.67 | 5.28 | 6.38 | 66.57 | 5.41 | 6.35 |
| 175 | C$_{23}$H$_{20}$Cl$_2$N$_2$O$_2$S | H$_2$ | S | 3,6-(CH$_3$)$_2$,5-Cl | 4-Cl | 2-CH$_3$ | 60.13 | 4.39 | 6.10 | 60.39 | 4.69 | 6.13 |
| 176 | C$_{24}$H$_{21}$Cl$_3$N$_2$O$_2$S | 2-Cl | S | 3,6-(CH$_3$)$_2$,5-Cl | 3-CH$_3$—4-Cl | 5-CH$_3$ | 56.76 | 4.17 | 5.52 | 56.96 | 4.25 | 5.57 |
| 177 | C$_{24}$H$_{21}$BrCl$_2$N$_2$O$_2$S | 2-Cl | S | 3,6-(CH$_3$)$_2$,5-Cl | 2-CH$_3$—4-Br | 3-CH$_3$ | 52.19 | 3.83 | 5.07 | 52.61 | 3.92 | 4.91 |
| 178 | C$_{23}$H$_{20}$BrClN$_2$O$_2$S | 2-Cl | S | 3-CH$_3$ | 2-CH$_3$—4-Br | 3-CH$_3$ | 54.83 | 4.00 | 5.56 | 54.98 | 4.18 | 5.57 |
| 179 | C$_{20}$H$_{20}$Cl$_2$N$_2$O$_2$S | 2-Cl | S | 3-CH$_3$ | 2-CH$_3$—4-Cl | 5-CH$_3$ | 60.13 | 4.39 | 6.10 | 60.62 | 4.61 | 6.13 |
| 180 | C$_{26}$H$_{25}$BrCl$_2$N$_2$O$_2$S | 2-Cl | S | 3,6-(CH$_3$)$_2$,5-Cl | 4-Br | 2-s-butyl | 53.81 | 4.34 | 4.83 | 54.16 | 4.36 | 5.20 |
| 181 | C$_{24}$H$_{21}$ClF$_2$N$_2$O$_2$S | 2,6-F$_2$ | S | 3,6-(CH$_3$)$_2$,5-Cl | 2-CH$_3$ | 4-CH$_3$ | 60.69 | 4.46 | 5.90 | 60.35 | 4.57 | 5.98 |
| 182 | C$_{24}$H$_{19}$Cl$_2$N$_3$O$_3$ | 2-Cl | O | 3,6-(CH$_3$)$_2$,5-Cl | 4-CN | 2-CH$_3$ | 61.55 | 4.09 | 8.97 | 61.68 | 4.48 | 8.32 |
| 183 | C$_{24}$H$_{18}$ClF$_2$N$_3$O$_3$ | 2,6-F$_2$ | O | 3,6-(CH$_3$)$_2$,5-Cl | 4-CN | 2-CH$_3$ | 61.35 | 3.86 | 8.94 | 63.16 | 4.42 | 8.35 |
| 184 | C$_{25}$H$_{21}$Cl$_2$N$_3$O$_3$ | 2-Cl | O | 3,6-(CH$_3$)$_2$,5-Cl | 4-CN,5-CH$_3$ | 2-CH$_3$ | 62.25 | 4.39 | 8.71 | 62.21 | 4.59 | 8.50 |
| 185 | C$_{25}$H$_{20}$ClF$_2$N$_3$O$_3$ | 2,6-F$_2$ | O | 3,6-(CH$_3$)$_2$,5-Cl | 4-CN,5-CH$_3$ | 2-CH$_3$ | 62.06 | 4.17 | 8.68 | 61.72 | 4.46 | 8.49 |
| 186 | C$_{26}$H$_{23}$ClF$_2$N$_2$O$_5$ | 2,6-F$_2$ | O | 3,6-(CH$_3$)$_2$,5-Cl | 4-CO$_2$C$_2$H$_5$ | 2-CH$_3$ | m.p. 176~179° C. | | | | | |
| 187 | C$_{26}$H$_{24}$Cl$_2$N$_2$O$_5$ | 2-Cl | O | 3,6-(CH$_3$)$_2$,5-Cl | 4-CO$_2$C$_2$H$_5$ | 2-CH$_3$ | m.p. 188~190° C. | | | | | |

Certain representative examples of the new compounds were evaluated to determine their pesticidal activity against certain insects, including a caterpiller and a beetle. The new compounds were also tested for phtotoxicity on important economic crops including bean, soybean, corn, tomato and cotton. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of an alkylphenoxy polyethoyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Southern Armyworm Leaf Spray Bait Test

Larvae of the southern armyworm (*Spodoptera eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standrd height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Tobacco Budworm and Cotton Bollworm Leaf Spray Bait Test

Second instar larvae of the tobacco budworm (weighting about 4.5 mg) (*Heliothis virescens*, F.) and the cotton bollworm (weighing about 2.5 mg) (*Heliothis zea*, (Boddie)), obtained commercially and reared on artificial diet at a temperature of 80°±5° F. and a relative humidity of 50±5 percent, constituted the test insects.

Using a procedure similar to the above, but substituting cotten plants for snapbeans, treated and dried cotton leaves were introduced into 9 cm Petri dishes which were organized in to groups of 10-dish sets. One randomly selected larvae was introduced into each dish of a ten dish set and the dishes were closed. The closed dishes were labelled and held at 80°±5° F. for five days.

The biological properties of certain representative examples of the compounds of this invention are set forth in Table II below.

TABLE II

Biological Properties of Representative Benzoyl Ureas

| Example | Activity 500 ppm | |
|---|---|---|
| | SAW[1] | MBB[2] |
| 1 | A | A |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | A |
| 13 | A | A |
| 14 | A | A |
| 15 | A | A |
| 16 | A | A |
| 17 | A | A |
| 18 | A | A |
| 19 | A | A |
| 20 | A | A |
| 21 | A | A |
| 22 | A | A |
| 23 | A | A |
| 24 | A | A |
| 25 | A | A |
| 26 | A | A |
| 27 | A | A |
| 28 | A | A |
| 29 | A | A |
| 30 | A | A |
| 31 | A | A |
| 32 | A | A |
| 33 | A | A |
| 34 | A | A |
| 35 | A | A |
| 36 | A | A |
| 37 | A | A |
| 38 | A | A |
| 39 | A | A |
| 40 | A | A |
| 41 | A | A |
| 42 | A | A |
| 43 | A | A |
| 44 | A | A |
| 45 | A | A |
| 46 | A | A |
| 47 | A | A |
| 48 | A | A |
| 49 | A | A |
| 50 | A | A |
| 53 | A | A |
| 54 | A | A |
| 55 | A | A |
| 56 | A | A |
| 57 | A | A |
| 58 | A | A |
| 59 | A | A |
| 60 | A | A |
| 61 | A | A |
| 62 | A | A |
| 63 | A | A |
| 64 | A | A |
| 66 | A | A |
| 67 | C | A |
| 68 | C | A |
| 69 | A | A |
| 70 | A | A |
| 71 | C | A |
| 72 | C | A |
| 73 | C | A |
| 74 | A | A |
| 75 | A | A |
| 76 | A | A |
| 77 | A | A |
| 78 | A | A |
| 79 | A | A |
| 80 | A | A |
| 81 | A | A |

TABLE II-continued
Biological Properties of Representative Benzoyl Ureas

| | Activity 500 ppm | |
|---|---|---|
| Example | SAW[1] | MBB[2] |
| 82 | A | A |
| 83 | A | A |
| 84 | A | A |
| 85 | A | A |
| 86 | A | A |
| 87 | A | A |
| 88 | A | A |
| 89 | A | A |
| 90 | C | A |
| 91 | A | A |
| 92 | C | A |
| 93 | A | A |
| 94 | A | A |
| 96 | A | A |
| 97 | A | C |
| 98 | A | A |
| 99 | A | A |
| 101 | B | B |
| 102 | A | A |
| 103 | A | A |
| 104 | A | A |
| 105 | A | A |
| 106 | A | B |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | A | A |
| 118 | A | A |
| 119 | A | C |
| 120 | A | A |
| 121 | A | C |
| 122 | A | A |
| 123 | A | A |
| 124 | A | A |
| 125 | A | A |
| 126 | A | A |
| 127 | A | A |
| 128 | A | A |
| 129 | A | A |
| 130 | A | A |
| 131 | A | A |
| 132 | A | A |
| 133 | A | A |
| 134 | A | A |
| 135 | A | A |
| 136 | A | A |
| 137 | A | A |
| 138 | A | A |
| 139 | A | A |
| 140 | A | A |
| 141 | A | A |
| 142 | A | A |
| 143 | A | A |
| 144 | A | A |
| 145 | A | A |
| 146 | A | A |
| 147 | A | A |
| 148 | A | A |
| 149 | A | A |
| 150 | A | A |
| 151 | A | A |
| 152 | A | A |
| 153 | A | A |
| 154 | A | A |
| 155 | A | A |
| 156 | A | A |
| 157 | A | A |
| 158 | A | A |
| 159 | A | A |
| 160 | A | A |
| 161 | A | A |
| 162 | A | A |
| 163 | A | A |
| 164 | A | A |
| 165 | A | A |
| 166 | A | A |
| 167 | A | A |
| 168 | A | A |
| 169 | A | A |
| 170 | A | A |
| 172 | A | A |
| 174 | A | A |
| 175 | A | A |
| 176 | C | A |
| 177 | A | A |
| 178 | A | A |
| 179 | A | A |
| 180 | A | C |
| 181 | A | A |
| 182 | A | A |
| 183 | A | A |

[1]Southern Armyworm
[2]Mexican Bean Beetle
[3]Code = A = Complete control  B = Moderate control  C = No control

EXAMPLES 212–217

In order to demonstrate the enhanced biological activity against the Southern Armyworm, representative benzoyl ureas were compared with known products. The results are set forth in Table III below:

TABLE III
Comparison Of Representative Benzoyl Ureas With Closely Related Prior Art Compounds Against Southern Armyworm

| Compound | Application rate (ppm) | Percent Control after 5 days |
|---|---|---|
| 1-(4-chlorophenyl)-3-(2,6-difluorobenzoyl)urea[1] | 10 | 100 |
| | 5 | 40 |
| 1-[4-(4-methylphenylthio)phenyl]-3-(2,6-dichlorobenzoyl)urea[2] | 500 | 40 |
| | 125 | 30 |
| | 31 | 10 |
| 1-[4-(2,4-dimethylphenoxy)-3-chlorophenyl]-3-(2-chlorobenzoyl)urea[3] | 125 | 100 |
| | 31 | 30 |
| | 8 | 20 |
| 1-[4-(2,4-dimethylphenoxy)-3,6-dimethyl-5-chlorophenyl]-3-(2-chlorobenzoyl)urea (Example #8) | 2 | 100 |
| | 1 | 100 |
| 1-[4-(2,4-dimethylphenoxy)-3,6-dimethyl-5-chlorophenyl]-3-(2-chlorobenzoyl)thiourea (Example #16) | 2 | 100 |
| | 1 | 90 |
| 1-[4-(2,4-dimethylphenoxy)3,5-dimethylphenyl]-3-(2,6-diflurorbenzoyl)urea (Example #4) | 8 | 100 |
| | 2 | 100 |

[1]Dimilin ®, a known compound.
[2]a prior art compound. Ger. Offen 2,901,334.
[3]a prior art compound. Ger. Offen. DE 3,104,407 (EP 57-888)

EXAMPLES 218–220

In order to demonstrate the enhanced biological activity against Heliothis, representative benzoyl ureas were compared with known products. The results are set forth in Table IV and V below:

TABLE IV

Comparison Of Representative Benzoyl Ureas
With Closely Related Prior Art
Compounds Against Heliothis zea

| Compound | LD$_{50}$ (ppm) Heliothis zea |
|---|---|
| 1-(4-chlorophenyl)-3-(2,6-difluorobenzoyl)urea[1] | 500 |
| 1-[4-(4-methylphenylthio)phenyl]-3-(2,6-dichlorobenzoyl)urea[2] | >100 |
| 1-[4-(2,4-dimethylphenoxy)-3-chlorophenyl]-3-(2,6-difluorobenzoyl)urea[3] | >100 |
| 1-[4-(2,4,5-trimethylphenoxy)-3,6-dimethyl-5-chlorophenyl]-3-(2,6-difluorobenzoyl)urea (Example #159) | 0.4 |
| 1-[4-(2,5-dimethyl-4-chlorophenoxy)-3,6-dimethyl-5-chlorophenyl]-3-(2,6-difluorobenzoyl)urea (Example #145) | 0.7 |

[1]Dimilin ®, a known compound
[2]a prior art compound. Ger. Offen 2,901,334.
[3]a prior art compound. Ger. Offen. DE 3,104,407 (EP 57-888)

TABLE V

Comparison Of Representative Benzoyl Ureas
With Closely Related Prior Art
Compounds Against Heliothis virescens

| Compound | LD$_{50}$ (ppm) Heliothis virescens |
|---|---|
| 1-(4-chlorophenyl)-3-(2,6-difluorobenzoyl)urea[1] | 31 |
| 1-[4-(4-methylphenylthio)phenyl]-3-(2,6-dichlorobenzoyl)urea[2] | >100 |
| 1-[4-(2,4-dimethylphenoxy)-3-chlorophenyl]-3-(2,6-difluorobenzoyl)urea[3] | >100 |
| 1-[4-(2,5-dimethyl-4-chlorophenoxy)-3,6-dimethyl-5-chlorophenyl]-3-(2,6-difluorobenzoyl)urea (Example #145) | 0.63 |
| 1-[4-(2-methyl-4-t-butylphenoxy)-3,6-dimethyl-5-chlorophenyl]-3-(2,6-difluorobenzoyl)urea (Example #57) | 2.4 |

[1]Dimilin ®, a known compound
[2]a prior art compound. Ger. Offen 2,901,334
[3]a prior art compound. Ger. Offen. DE 3,104,407 (EP 57-888)

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A compound having the formula 1-[4-(2,4-dimethylphenoxy)-3,6-dimethyl-5-chlorophenyl]-3-(2-chlorobenzoyl) urea.

2. A compound having the formula 1-[4-(2,4-dimethylphenoxy-)-3,6-dimethyl-5-chlorophenyl]-3-(2,6-difluorobenzoyl) urea.

3. An insecticide composition comprising an acceptable carrier and an insecticidally effective amount of the compound of claim 1.

4. An insecticide composition comprising an acceptable carrier and an insecticidally effective amount of the compound of claim 2.

5. A method of controlling insects which comprises subjecting said insects to an insecticidally effective amount of the compound of claim 1.

6. A method of controlling insects which comprises subjecting said insects to an insecticidally effective amount of the compound of claim 2.